United States Patent
Sakamoto

(10) Patent No.: US 10,729,425 B2
(45) Date of Patent: Aug. 4, 2020

(54) SUTURE DEVICE

(71) Applicant: OLYMPUS CORPORATION, Tokyo (JP)

(72) Inventor: Tetsuyuki Sakamoto, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 362 days.

(21) Appl. No.: 15/866,612

(22) Filed: Jan. 10, 2018

(65) Prior Publication Data
US 2018/0140294 A1 May 24, 2018

Related U.S. Application Data

(63) Continuation of application No. PCT/JP2016/061198, filed on Apr. 6, 2016.

(30) Foreign Application Priority Data

Jul. 29, 2015 (JP) .................................. 2015-149588

(51) Int. Cl.
A61B 17/04 (2006.01)
A61B 17/062 (2006.01)
(Continued)

(52) U.S. Cl.
CPC ...... A61B 17/0469 (2013.01); A61B 17/0491 (2013.01); A61B 17/062 (2013.01);
(Continued)

(58) Field of Classification Search
CPC ............ A61B 17/0469; A61B 17/0491; A61B 17/062; A61B 17/0625; A61B 2017/0034; A61B 2017/06028
See application file for complete search history.

(56) References Cited

U.S. PATENT DOCUMENTS 5,814,054 A 9/1998 Kortenbach et al.
2003/0109889 A1 6/2003 Mercereau et al.
(Continued)

FOREIGN PATENT DOCUMENTS

AU 2009202354 A1 1/2010
CA 2668618 A1 12/2009
(Continued)

OTHER PUBLICATIONS

International Search Report dated Jul. 5, 2016 issued in PCT/JP2016/061198.

Primary Examiner — Elizabeth Houston
Assistant Examiner — Socrates L Boutsikaris
(74) Attorney, Agent, or Firm — Scully, Scott, Murphy & Presser, P.C.

(57) ABSTRACT

A suture device including: an elongated shaft member; a pair of gripping members; and a passing mechanism that transfers a suture needle between the gripping members, wherein the passing mechanism is provided with fitting holes provided in the individual gripping members and to which the suture needle is fitted, holding members that are inserted into recessed portions in outer circumferential surface of the suture needle by being pulled toward the proximal end sides thereof in directions that intersect axes of the individual fitting holes, a swing member that is provided so as to be swingable about an axis that is orthogonal to the longitudinal axis, a pair of tensile-force transmitting members that transmit tensile forces that cause the swing member to be swung, axial-force transmitting members that transmit axial forces associated with swinging of the swing member, and holdstate maintaining mechanism that maintains the holding members in the recessed portions.

4 Claims, 15 Drawing Sheets

(51) Int. Cl.
  *A61B 17/06* (2006.01)
  *A61B 17/00* (2006.01)
(52) U.S. Cl.
  CPC .. *A61B 17/0625* (2013.01); *A61B 2017/0034* (2013.01); *A61B 2017/06028* (2013.01)

(56) References Cited

U.S. PATENT DOCUMENTS

| | | |
|---|---|---|
| 2009/0084826 A1 | 4/2009 | Shah et al. |
| 2009/0312773 A1 | 12/2009 | Cabrera et al. |
| 2010/0163597 A1 | 7/2010 | Shah et al. |
| 2011/0040308 A1 | 2/2011 | Cabrera et al. |
| 2015/0230790 A1* | 8/2015 | Hashimoto ............ A61B 17/06 |
| | | 606/145 |

FOREIGN PATENT DOCUMENTS

| | | | |
|---|---|---|---|
| EP | 2042107 A1 | 4/2009 | |
| EP | 2133028 A2 | 12/2009 | |
| EP | 2889008 A1 | 7/2015 | |
| JP | 2001-500765 A | 1/2001 | |
| JP | 2005-511192 A | 4/2005 | |
| JP | 2009-082704 A | 4/2009 | |
| JP | 2010-005386 A | 1/2010 | |
| JP | 2014-030544 A | 2/2014 | |
| JP | 2015-061669 A | 4/2015 | |
| WO | WO 98/11829 A1 | 3/1998 | |
| WO | WO 03/049625 A1 | 6/2003 | |
| WO | WO 2014/030544 A1 | 2/2014 | |
| WO | WO-2014030544 A1 * | 2/2014 | ......... A61B 17/0625 |

* cited by examiner

SUTURE DEVICE

CROSS-REFERENCE TO RELATED APPLICATIONS

This is a Continuation Application of International Application No. PCT/JP2016/061198 filed on Apr. 6, 2016, which claims priority to Japanese Application No. 2015-149588 filed on Jul. 29, 2015. The contents of International Application No. PCT/JP2016/061198 and Japanese Application No. 2015-149588 are hereby incorporated by reference herein in its entirety.

TECHNICAL FIELD

The present invention relates to a medical suture device.

BACKGROUND ART

There is a known suture device for suturing tissue or the like in a body (see Japanese Translation of PCT International Application, Publication No. 2001-500765 and Japanese Unexamined Patent Application, Publication No. 2014-30544).

Such a suture device includes two gripping members that can be opened/closed at a distal end of an elongated shaft member that is inserted into the body of a patient. The gripping members are provided with a passing mechanism for passing a suture needle therebetween; by sandwiching a suture object between the two gripping members in a state in which the suture needle, to which a suture thread is attached, is held by one of the gripping members, the suture needle is made to penetrate the suture object; and, by passing the suture needle between the two gripping members in an alternating manner by means of the passing mechanism, the suture object is sutured.

SUMMARY OF INVENTION

An aspect of the present disclosure is a suture device including: an elongated shaft member that extends along a longitudinal axis and that is flexible and tubular; a pair of two gripping members that are disposed at a distal end side of the elongated shaft member in a pivotable manner about a pivot orthogonal to the longitudinal axis so that the two gripping members are opened/closed; and a passing mechanism configured to pass a suture needle between the gripping members, the suture needle to which a suture thread is attached, wherein the passing mechanism comprises: fitting holes that are respectively provided in the individual gripping members along opening/closing directions thereof and into which the suture needle is fitted; holding members which are respectively provided in the gripping members so as to be movable in the directions that intersect axes of the individual fitting holes, and each of which is inserted into a recessed portion provided in an outer circumferential surface of the suture needle fitted into the fitting hole when the holding member is pulled toward a proximal end side; a swing member which is provided at a position that is closer to a proximal-end side of the elongated shaft member than the pivot of the gripping members so as to be swingable about a swing axis that is orthogonal to the longitudinal axis; a pair of tensile-force transmitting members which extend inside the elongated shaft member and which transmit tensile force for swinging the swing member; axial-force transmitting members which have flexibility, which is disposed between the swing member and the respective holding members, and which respectively transmit axial force based on swing of the swing member in order to oppositely move the holding members; and a hold-state maintaining mechanism that maintains the holding members in a state in which one of the holding members is inserted into the recessed portion regardless of pivoting of the gripping members.

DESCRIPTION OF EMBODIMENT

A suture device 1 according to an embodiment of the present invention will be described below with reference to the drawings.

Figure 1:
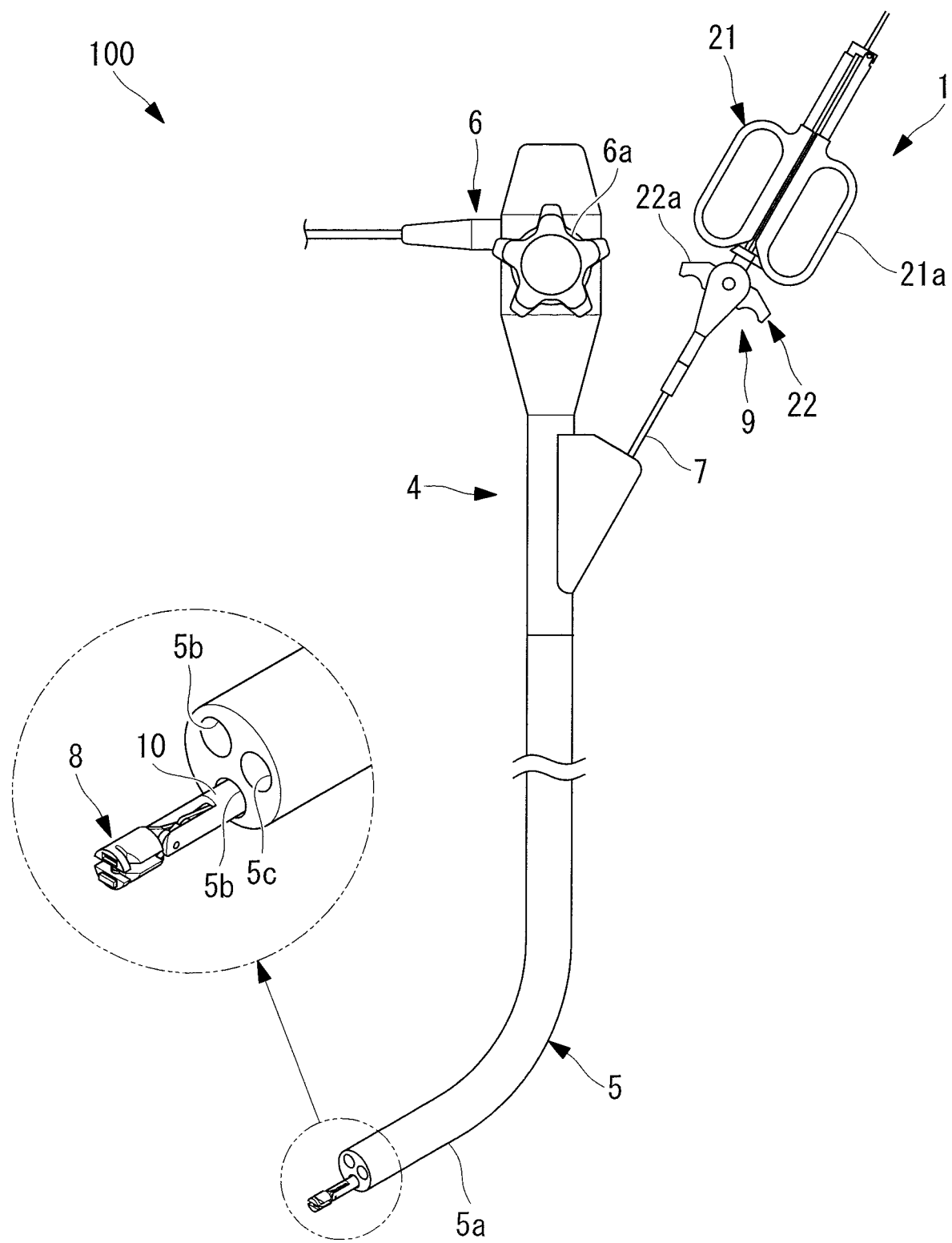
FIG. 1 is an overall configuration diagram showing a suture system provided with a suture device according to an embodiment of the present invention.

FIG. 1 shows a suture system 100 in which the suture device 1 according to this embodiment is employed.

Figure 3:
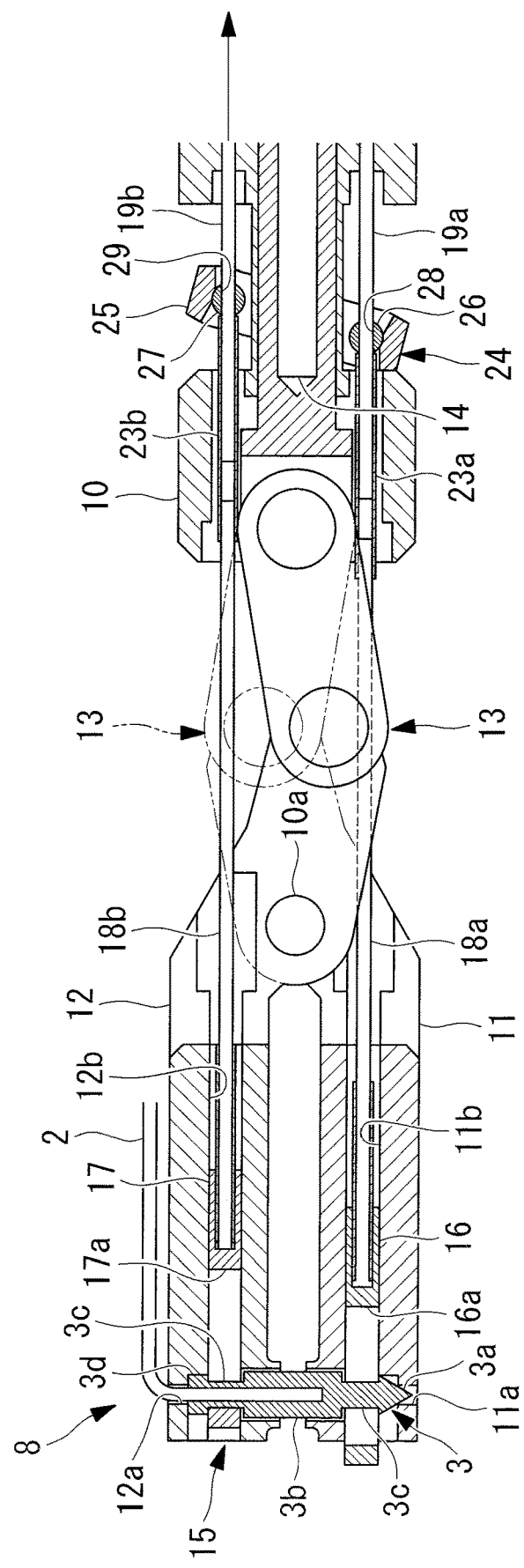
FIG. 3 is a longitudinal cross-sectional view of the treatment portion in FIG. 2.
Figure 4A:
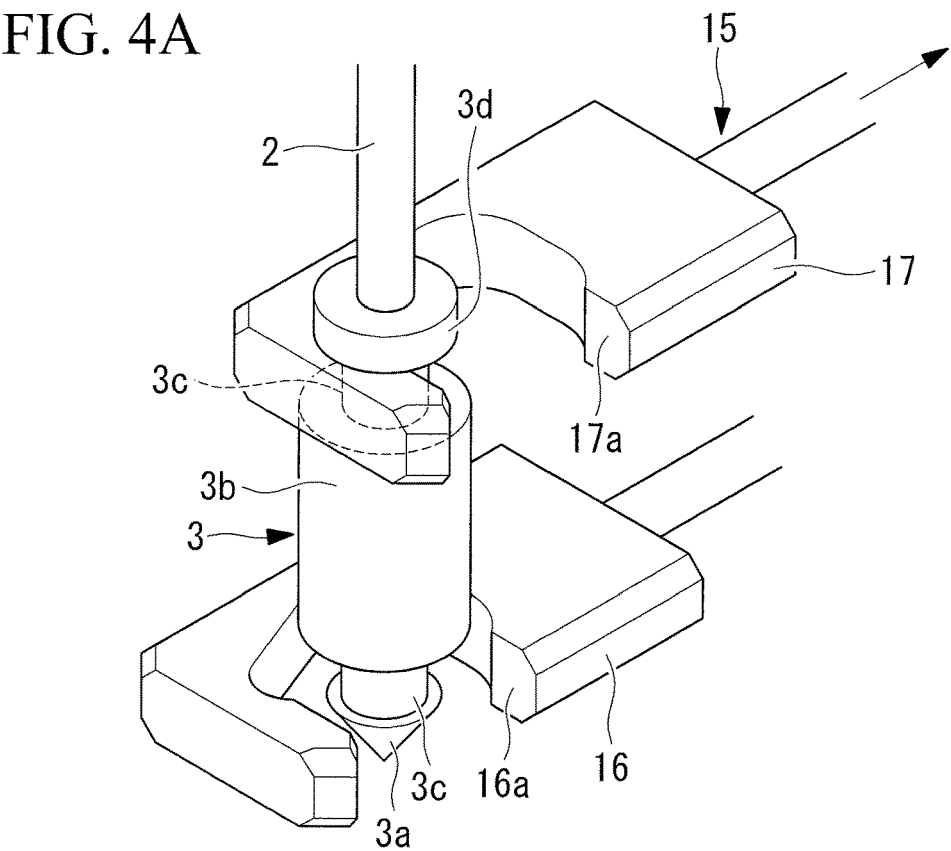
FIG. 4A is a diagram showing the relationship between holding members of the treatment portion in FIG. 2 and a suture needle, and is a perspective view showing a state in which the suture needle is held by the holding member on a flange-portion side.
Figure 4B:
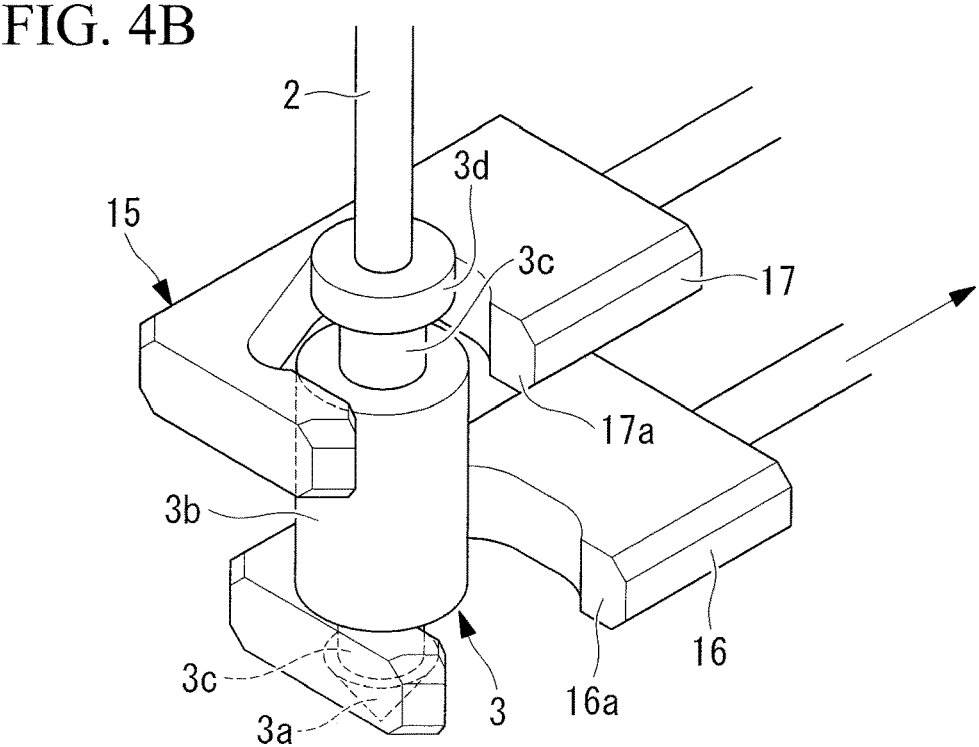
FIG. 4B is a diagram showing the relationship between the holding members of the treatment portion in FIG. 2 and the suture needle, and is a perspective view showing a state in which the suture needle is held by the holding member on a pointed end portion side.

As shown in FIGS. 3, 4A and 4B, this suture system 100 is a system with which tissue A is sutured by using a suture needle 3, to which a suture thread 2 is fixed at one end thereof and that has a pointed end portion 3a at the other end thereof. As shown in FIG. 1, the suture system 100 is provided with an endoscope 4 and the suture device 1 according to this embodiment.

The endoscope 4 is a publically known endoscope and is provided, on a proximal-end side of an elongated, flexible insertion portion 5, with a manipulating portion 6 that is manipulated by an operator. A distal-end portion of the insertion portion 5 is provided with a bending portion 5a that can be bent by manipulating a knob 6a on the manipulating portion 6.

The insertion portion 5 of the endoscope 4 is provided with two channels 5b that penetrate through the insertion portion 5 in a longitudinal direction and that are provided with openings in distal-end surfaces thereof. In the figure, reference symbol 5c indicates an observation optical system. The number of channels 5b may be one, three, or more.

The suture device 1 according to this embodiment is provided with: an elongated shaft member 7 that is a long, flexible and tubular having an external size that allows insertion thereof into the channel 5b; a treatment portion 8 provided at a distal end of the elongated shaft member 7; and a manipulating portion 9 provided at a proximal-end of the elongated shaft member 7.

Figure 2:
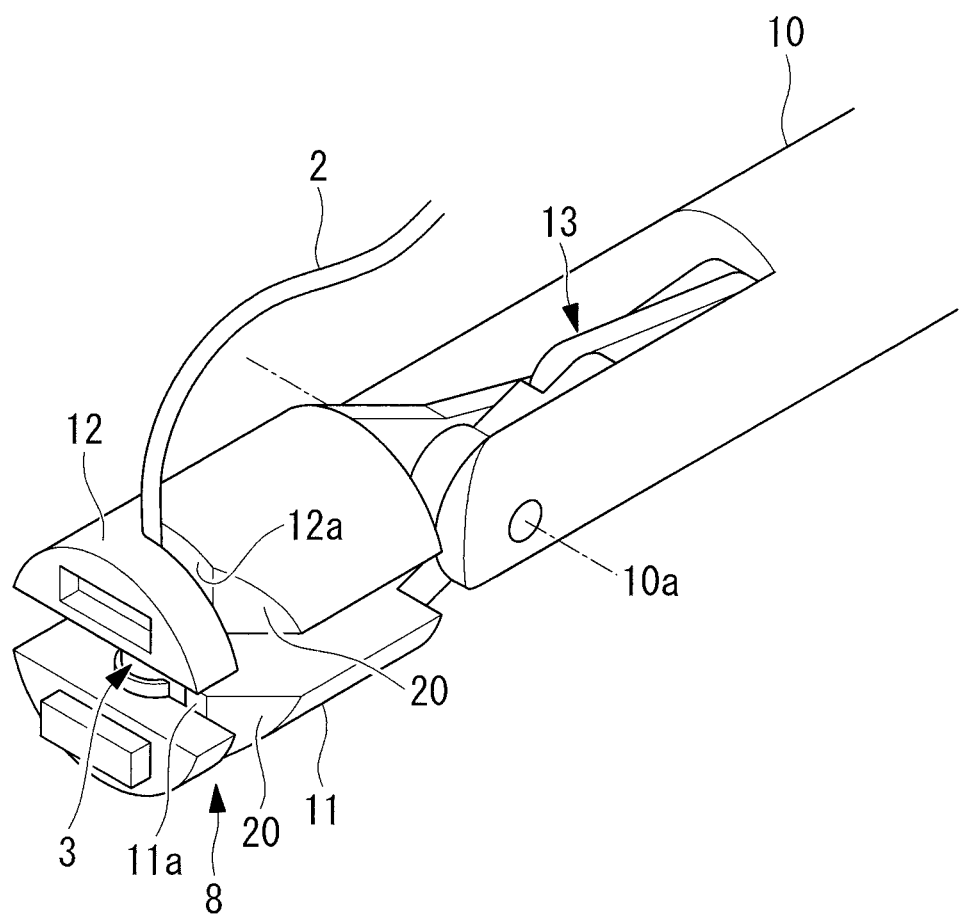
FIG. 2 is a perspective view showing a treatment portion of the suture device in FIG. 1.

As shown in FIG. 2, the treatment portion 8 is provided with: a base 10 that is fixed to the distal end of the elongated shaft member 7; and two gripping members 11, 12 that are attached to the base 10 so as to be pivotable about an axis (pivot) 10a that is orthogonal to a longitudinal axis of the elongated shaft member 7.

Figure 8:
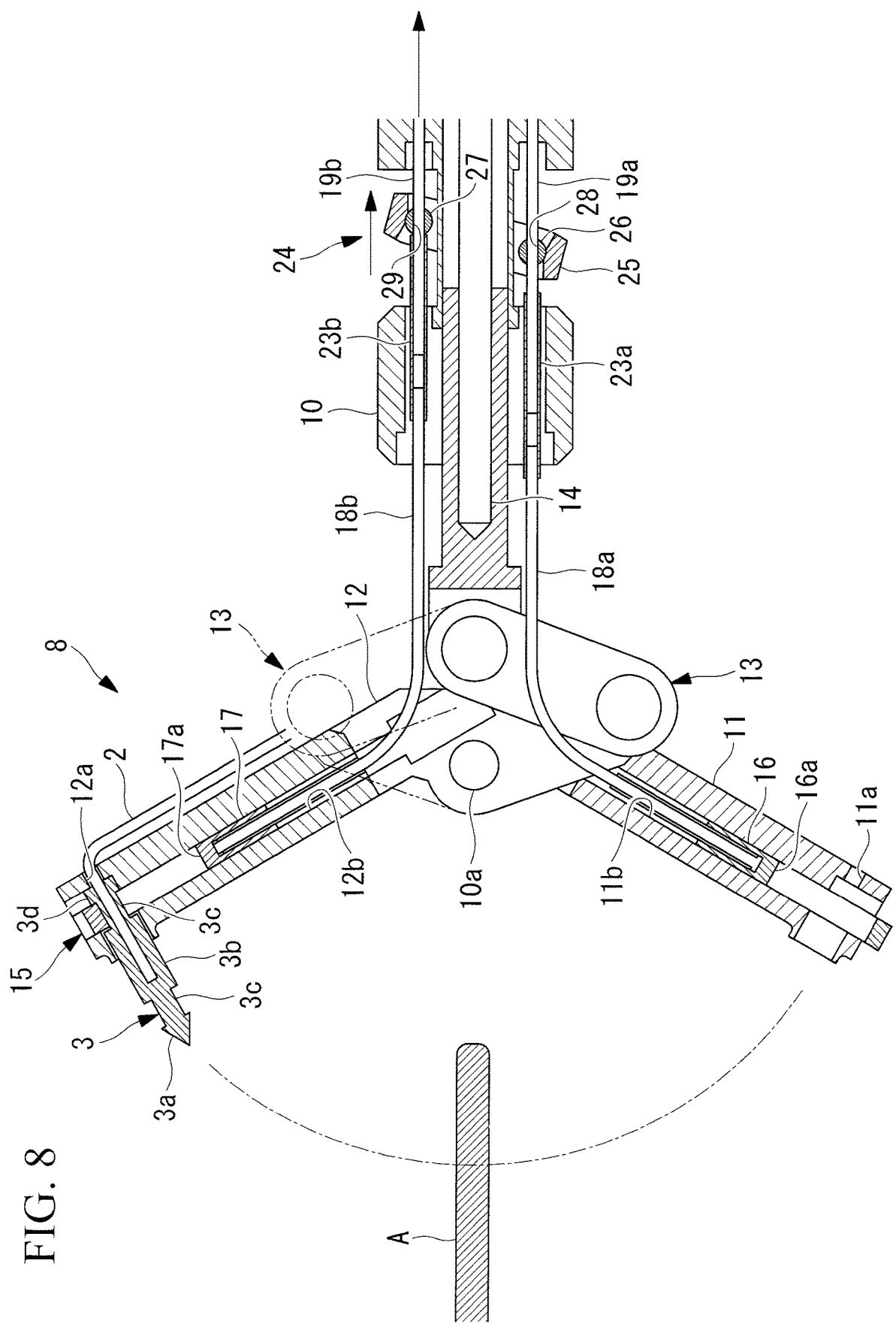
FIG. 8 is a longitudinal cross-sectional view showing a state in which two gripping members of the treatment portion in FIG. 2 are open.

As shown in FIG. 3, the two gripping members 11, 12 are individually connected to an opening/closing wire 14 via linkages 13. By doing so, as shown in FIGS. 2 and 3, when the opening/closing wire 14 is pulled toward the proximal-end side thereof, the two gripping members 11, 12 are placed in closed positions at which both members extend substantially parallel to each other along the longitudinal axis, and, as shown in FIG. 8, by pushing out the opening/closing wire 14 to the distal-end side from the proximal-end side thereof, the two gripping members 11, 12 are placed in open positions by being pivoted. In FIGS. 3 and 8 to 10, in order to simplify the illustration, the linkage 13 connected to the gripping member 11 is indicated by chain lines.

The two gripping members 11, 12 are provided with a passing mechanism 15 for passing the suture needle 3 therebetween.

Here, the suture needle 3 used in the suture device 1 according to this embodiment will be described.

As shown in FIGS. 3, 4A, and 4B, the suture needle 3 is formed in a substantially columnar shape and has the conical pointed end portion 3a on one end thereof, and the suture thread 2 is fixed to the other end thereof by means of adhesion or the like. At a center portion of the suture needle 3 in the longitudinal direction thereof, a large-diameter portion 3b having the largest external size is provided over a predetermined length, and, on both sides of the large-diameter portion 3b in the longitudinal axial direction, recessed portions 3c that are recessed in axial directions around the entire circumference are provided at positions on either side of the large-diameter portion 3b. The pointed end portion 3a and a flange portion 3d, which protrude radially farther outward than the recessed portions 3c do, and are provided at portions closer to end portions in the axial direction than the recessed portions 3c are.

As shown in FIG. 3, the passing mechanism 15 is provided with: through-holes (fitting holes) 11a, 12a that are provided in the vicinity of the distal-end portions of the two gripping members 11, 12, which are pivoted, so as to pass therethrough in the pivoting direction (opening/closing direction); holding members 16, 17 that are disposed, so as to be movable in longitudinal directions, inside guide holes 11b, 12b that are provided inside the individual gripping members 11, 12 in longitudinal directions that are orthogonal to the through-holes 11a, 12a; and distal-end wires (axial-force transmitting members) 18a, 18b and driving wires (tensile-force transmitting members) 19a, 19b that drive the holding members 16, 17.

As shown in FIGS. 4A and 4B, the holding members 16, 17 are flat-plate members that are translated in the longitudinal directions, are provided with opening portions 16a, 17a that are provided in directions that intersect the moving directions thereof (sideward), and are formed in a hook shape as a whole. The plate thicknesses of the holding members 16, 17 are configured to be less than the widths of the recessed portions 3c on the suture needle 3. In addition, the opening portions 16a, 17a of the holding members 16, 17 are formed so as to have sizes through which the flange portion 3d and the pointed end portion 3a can pass.

As shown in FIG. 3, the distal-end wires 18a, 18b and the driving wires 19a, 19b are connected with each other by means of connecting members (stopper portions) 23a, 23b.

As compared to the driving wires 19a, 19b, the distal-end wires 18a, 18b possess sufficiently high rigidity, and are capable of transmitting both tensile forces and compressive forces (axial forces).

The distal ends of the distal-end wires 18a, 18b are fixed to the proximal-end sides of the holding members 16, 17, and the proximal-end sides of the driving wires 19a, 19b are fixed to the manipulation portion 9 on the proximal-end side of the elongated shaft member 7. When tensile forces are exerted on the driving wires 19a, 19b by manipulating the manipulation portion 9, the tensile forces are transmitted to the holding members 16, 17 via the connecting members 23a, 23b and the distal-end wires 18a, 18b, thus pulling the holding members 16, 17 and causing the holding members 16, 17 to be moved toward the proximal-end sides thereof.

The passing mechanism 15 is provided with a swing member 24 that is disposed at a position closer to the proximal end side than the pivot 10a of the two gripping members 11 and 12 is, and that is disposed so as to be swingable about a swing axis 24a that is orthogonal to the longitudinal axis of the elongated shaft member 7.

Figure 5:
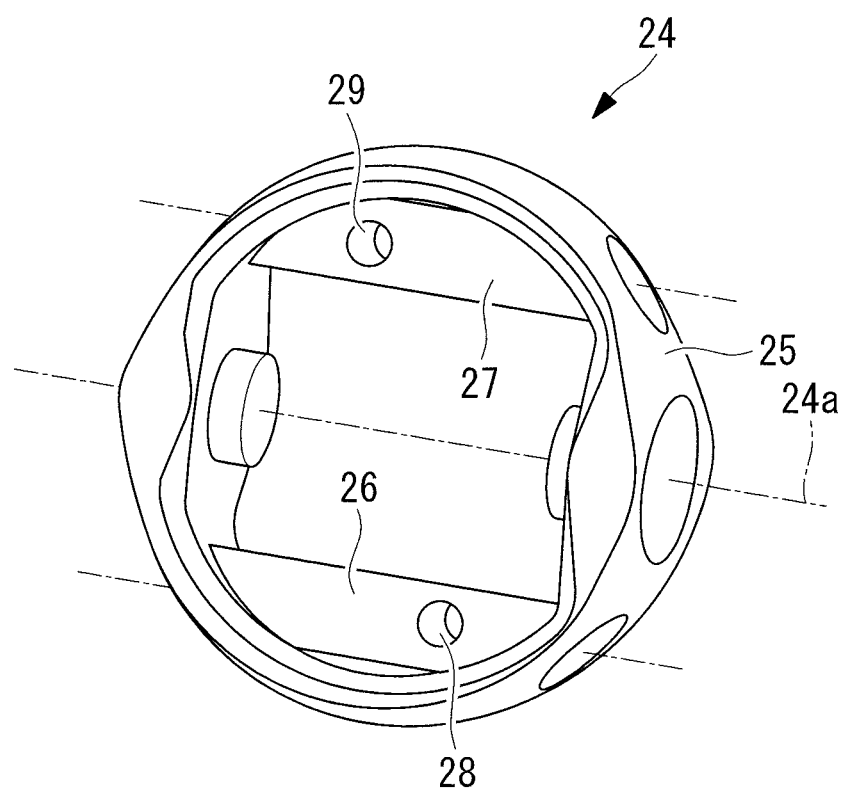
FIG. 5 is a perspective view showing a swing member provided in a passing mechanism of the suture device in FIG. 2.

As shown in FIGS. 3 and 5, the swing member 24 is provided with: a ring-shaped member 25; and two columnar members 26, 27 that are disposed inside the ring-shaped member 25 and that extend parallel to the swing axis 24a on either side of the swing axis 24a. The individual columnar members 26, 27 are attached to the ring-shaped member 25 so as to be rotatable about the longitudinal axes thereof. In addition, the individual columnar members 26, 27 are provided with through-holes 28, 29 that pass through the columnar members 26, 27 in the radial directions, and the driving wires 19a, 19b are made to pass through the through-holes 28, 29.

The diameters of the through-holes 28, 29 are set to be greater than external diameters of the driving wires 19a, 19b and less than external diameters of the connecting members 23a, 23b. When tensile forces are exerted on the driving wires 19a, 19b and the driving wires 19a, 19b are moved toward the proximal end sides thereof, the connecting members 23a, 23b cannot pass through the through-holes 28, 29 and are caught at side surfaces of the columnar members 26, 27, which causes the columnar members 26, 27 to be pulled toward the proximal end side of the elongated shaft member 7, thereby causing the ring-shaped member 25 to be swung about the swing axis 24a.

At this time, by being rotated about the longitudinal axes thereof, the columnar members 26, 27 maintain the state in which the through-holes 28, 29 are parallel to the longitudinal directions of the driving wires 19a, 19b.

As shown in FIG. 3, when one driving wire 19b pulls one columnar member 27 toward the proximal end side, thus causing the swing member 24 to swing, the other columnar member 26 is pushed out toward the distal end side, and, consequently, the connecting member 23a of the other driving wire 19a, which passes through the through-hole 28 of the columnar member 26, which has been pushed out, is caught at the side surface of the columnar member 26, and thus, the connecting member 23a is pushed out toward the distal end side. When the connecting member 23a is pushed out, the connecting member 23a causes a compressive force to act on the other distal-end wire 18a connected to the other driving wire 19a in the direction in which the distal-end wire 18a is pushed toward the distal end side. Because the distal-end wire 18a possesses a sufficiently high rigidity, the distal-end wire 18a transmits the compressive force without buckling, thus pushing out the holding member 16 at the distal end toward the distal end side. By doing so, it is possible to selectively switch between holding and releasing of the suture needle 3 by means of the two holding members 16, 17.

Figure 6A:
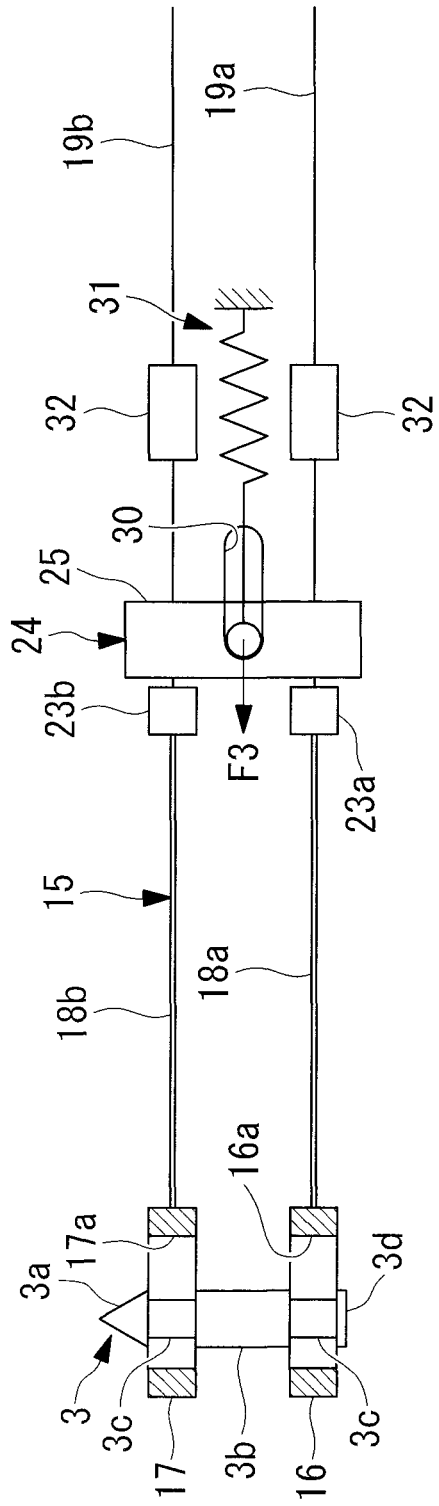
FIG. 6A is a diagram for explaining the operation of the passing mechanism of the suture device in FIG. 2, and is a schematic view showing a state in which no tensile force is acting on driving wires.
Figure 6B:
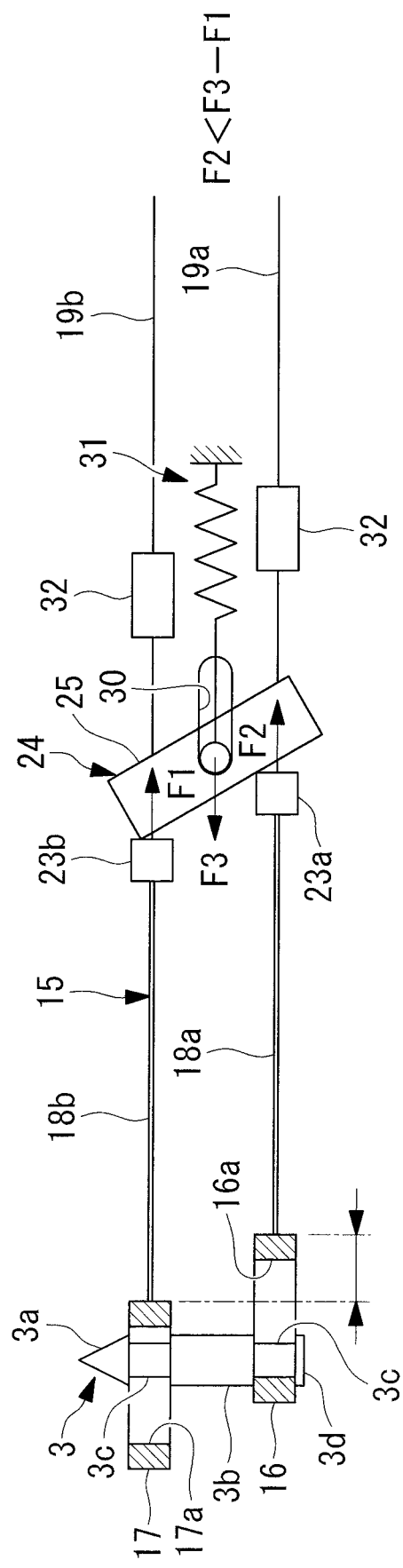
FIG. 6B is a diagram for explaining the operation of the passing mechanism of the suture device in FIG. 2, and is a schematic view showing a state in which the tensile forces that cause the swing member to be swung is acting on the driving wires.
Figure 6C:
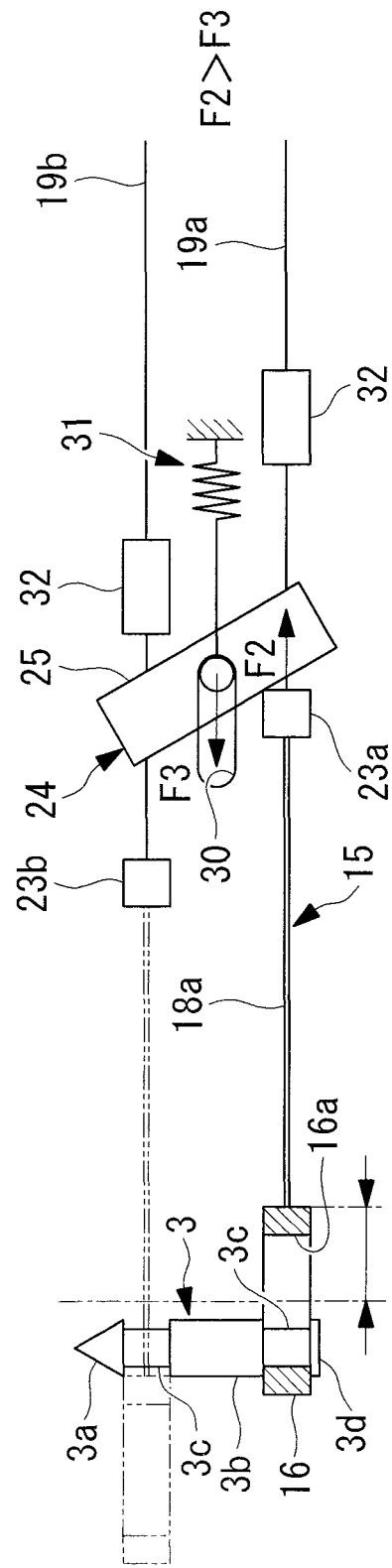
FIG. 6C is a diagram for explaining the operation of the passing mechanism of the suture device in FIG. 2, and is a schematic view showing a state in which the tensile forces that cause the swing member to be moved is acting on the driving wires.

As shown in FIGS. 6A to 6C, the swing member 24 is supported so as to be movable back and forth along a long hole provided in the base 10 along a longitudinal axial direction thereof. In addition, a compression coil spring (resilient member) 31 that biases the swing member 24 toward the distal end side along the long hole 30 is provided between the swing member 24 and the base 10. Even in a state in which the swing member 24 is disposed at the most distal end side of the long hole 30, the compression coil spring 31 biases the swing member 24 toward the distal end side by a biasing force F3. Note that another arbitrary resilient member may by employed instead of the compression coil spring 31.

Figure 7A:
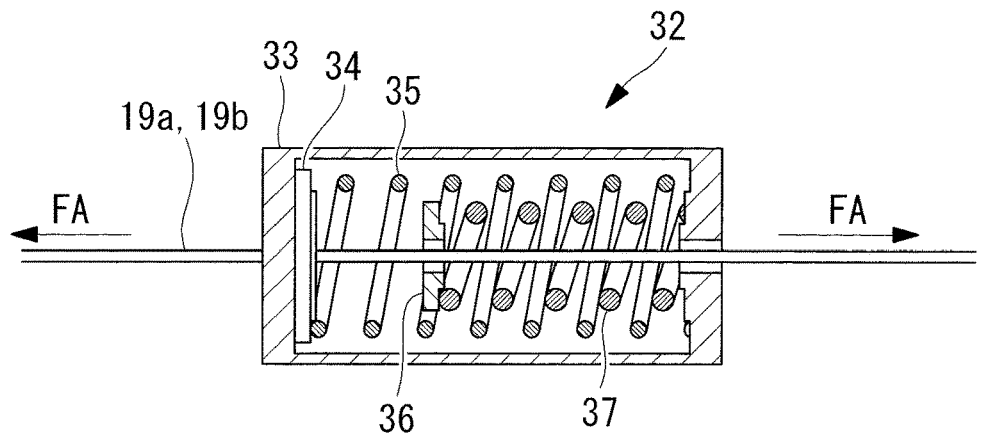
FIG. 7A is a longitudinal cross-sectional view showing a state in which a tensile force FA is acting on a tensile-force adjusting mechanism provided on the driving wire of the passing mechanism of the suture device in FIG. 2.
Figure 7B:
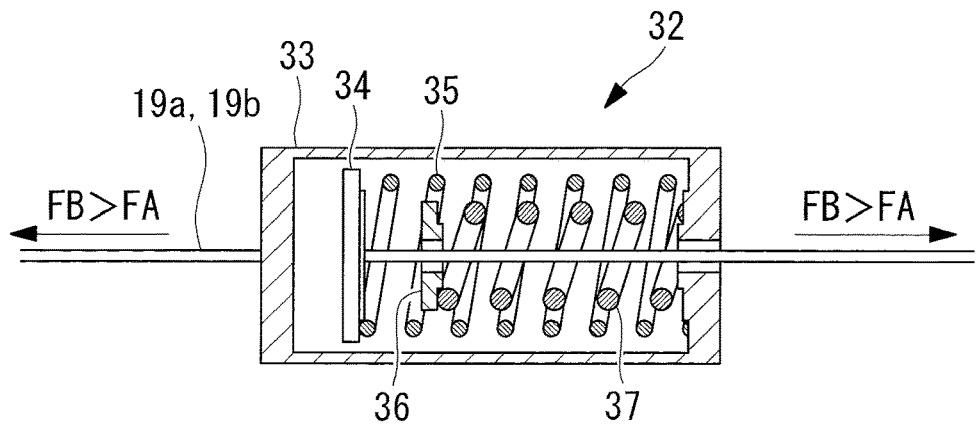
FIG. 7B is a longitudinal cross-sectional view showing a state in which a tensile force FB is acting on the tensile-force adjusting mechanism provided on the driving wire of the passing mechanism of the suture device in FIG. 2.
Figure 7C:
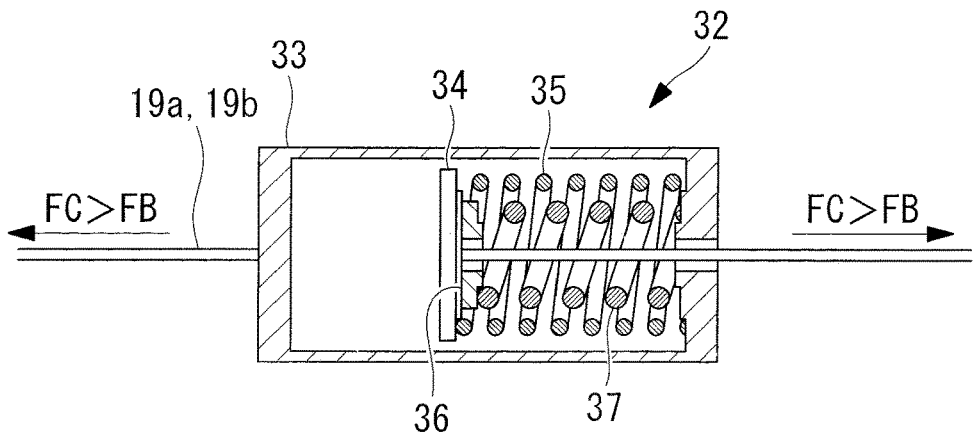
FIG. 7C is a longitudinal cross-sectional view showing a state in which a tensile force FC is acting on the tensile-force adjusting mechanism provided on the driving wire of the passing mechanism of the suture device in FIG. 2.

In this embodiment, the passing mechanism 15 is provided with tensile-force adjusting mechanisms (hold-state maintaining mechanism) 32 on the individual driving wires 19a, 19b. As shown in FIGS. 7A to 7C, the tensile-force adjusting mechanisms 32 are provided at intermediate positions of the driving wires 19a, 19b in the longitudinal directions, and are each provided with: a housing 33 connected to the driving wire 19a, 19b on the distal-end side; a first movable member (movable member) 34 that is connected to the driving wire 19a, 19b on the proximal end side and that is moved in the longitudinal direction inside the housing 33; a first compression coil spring (first compression spring) 35 that is disposed between the first movable member 34 and the housing 33; a second movable member 36 that abuts against the first movable member 34 in the process of compressing the first compression coil spring 35; and a second compression coil spring (second compression spring) 37 that is disposed between the second movable member 36 and the housing 33.

As shown in FIG. 7A, even in a state in which the first compression coil spring 35 is maximally extended, the tensile-force adjusting mechanism 32 can transmit a tensile force less than a predetermined tensile force FA. In addition, the tensile-force adjusting mechanism 32 is configured such that, as shown in FIG. 7B, the first compression coil spring 35 is resiliently deformed in the compressing direction when a tensile force FB that is greater than the tensile force FA acts on the driving wire 19a, 19b. Then, as shown in FIG. 7C, when the first compression coil spring 35 is resiliently deformed until reaching a position at which the first movable member 34 comes into contact with the second movable member 36, subsequently, the first compression coil spring 35 and the second compression coil spring 37 are simultaneously resiliently deformed in the compressing directions, thus making it possible to transmit an even greater tensile force FC.

As shown in FIG. 6A, in the state in which the compression coil spring 31 is maximally extended, the swing member 24 is biased toward the distal end by a biasing force F3. From this state, as shown in FIG. 6B, when a tensile force F2 acts on the other driving wire 19a, a reaction force F1 that the swing member 24 receives from the connecting member 23b when the swing member 24 pushes the connecting member 23b of one distal-end wire 18b toward the distal end is equal to the tensile force F2. Therefore, in the case in which the tensile force F2<F3−F1=F3/2, the compression coil spring 31 is not compressed any further, and the swing member 24 is not moved from the most distal-end position and is swung about the swing axis 24a at the position.

Subsequently, as shown in FIG. 6C, when the tensile force F2 exerted on the other driving wire 19a is increased until reaching a state in which the tensile force F2>F3, the compression coil spring 31 is compressed, and the swing member 24 is moved toward the proximal end side along the long hole 30 in the swung state.

At this time, one driving wire 19b is maintained in a stationary state at that position due to friction caused by contact or the like with an inner surface of the elongated shaft member 7.

In a state in which the suture needle 3 is fitted to the through-holes 11a, 12a of the gripping members 11, 12, the end portions of the suture needle 3 are made to pass through the opening portions 16a, 17a of the holding members 16, 17, and the recessed portions 3c thereof are disposed at positions aligned with the holding members 16, 17, when the holding members 16, 17 are moved toward the proximal end sides thereof by pulling the driving wires 19a, 19b, inner edges of the opening portions 16a, 17a on the distal-end sides thereof are inserted into the recessed portions 3c.

By doing so, the flange portion 3d or the pointed end portion 3a and the large-diameter portion 3b, which are disposed at positions at which the recessed portions 3c are sandwiched therebetween, engage with the holding members 16, 17 in the longitudinal direction of the suture needle 3, and are engaged so that the suture needle 3 does not move in the longitudinal directions in the through-holes 11a, 12a. In addition, the tensile forces exerted on the holding members 16, cause the inner edges of the holding members 16, 17 to press the recessed portions 3c in radial directions, and the suture needle 3 is pressed against the inner surfaces of the through-holes 11a, 12a, thus securing the suture needle 3 even more firmly by friction between those components.

As shown in FIG. 2, the gripping members 11, 12 are provided, at positions corresponding to the opening portions 16a, 17a of the holding members 16, 17 (laterally), with notches 20 that reach the through-holes 11a, 12a from outer surfaces of the gripping members 11, 12. Minimum widths of the notches 20 are set to be greater than the diameter of the suture thread 2 so that the suture thread 2 can be placed in/removed from the through-holes 11a, 12a through the notches 20. The notches 20 have a shape in which the openings thereof gradually increase toward the outer surfaces of the gripping members 11, 12 so as to facilitate placing/removing the suture thread 2 in/from the through-holes 11a, 12a.

As shown in FIG. 1, the manipulating portion 9 is provided with: an opening/closing manipulating portion 21 that is disposed on the proximal end side of the elongated shaft member 7 and that causes the two gripping members 11, 12 to perform an opening/closing operation; and a passing manipulating portion 22 for pulling the two driving wires 19a, 19b. The opening/closing manipulating portion 21 is provided with handles 21a formed like scissor grips, and the opening/closing wire 14 is pushed and pulled in the longitudinal axial directions by manipulating the handles 21a by opening/closing the handles 21a.

The operation of the thus-configured suture device 1 according to this embodiment will be described below.

In order to suture the tissue A in the body by using the suture device 1 according to this embodiment, first, the insertion portion 5 of the endoscope 4 is inserted into the body, and the distal end of the insertion portion 5 is disposed at a position at which a site to be sutured is placed in the viewing field area of the endoscope 4 while observing the body interior by using the observation optical system 5c positioned at the distal end of the insertion portion 5.

Regarding the suture device 1 on the other hand, as shown in FIG. 3, the two gripping members 11, 12 of the treatment portion 8 are closed by manipulating the handles 21a of the opening/closing manipulating portion 21, thus disposing the suture needle 3 so as to pass through the through-holes 11a and 12a of the two gripping members 11, 12 aligned in a straight line. Furthermore, by manipulating handles 22a of the passing manipulating portion 22, a tensile force is exerted on the other driving wire 19a that pulls the holding member 16 on the flange portion 3d side of the suture needle 3 toward the proximal end side.

At this time, the tensile force F2 exerted on the driving wire 19a is set to be the tensile force FA shown in FIG. 7A or the tensile force FB shown in FIG. 7B so as to achieve F2<F3/2.

By doing so, the tensile force is transmitted to the distal-end wire 18a connected to the driving wire 19a, the holding member 16 is pulled toward the base end, and thus, the connecting member 23a that connects the driving wire 19a and the distal-end wire 18a abuts against a side surface of the other columnar member 26 of the swing member 24. As a result, because the tensile force F2 in the driving wire 19a is exerted on the other columnar member 26, and the other columnar member 26 is pulled toward the proximal end side, the swing member 24 is swung about the swing axis 24a in position, thus pushing out said one columnar member 27 toward the distal end side.

By doing so, the tensile force exerted on the other driving wire 19a is transmitted to the other holding member 16 via the connecting member 23a and the other distal-end wire 18a, and other the holding member 16 is moved toward the proximal end side, thus inserting said holding member 16 into the recessed portion 3c on the flange portion 3d side of the suture needle 3. In addition, in association with this, the side surface of the columnar member 27 pushes out the connecting member 23b attached to said one driving wire 19b toward the distal end side, and the holding member 17 is moved toward the distal end side, thus achieving a state in which a portion of the suture needle 3 on the pointed end portion 3a side is released. In this embodiment, the handles 22a of the passing manipulating portion 22 are additionally manipulated, thus setting the tensile force F2 exerted on the other driving wire 19a to be the tensile force FC shown in FIG. 7C.

At this time, the tensile force F2 that acts on the other driving wire 19a is set so as to achieve F2>F3. In this state, even if the suture needle 3 is disposed in a state in which the suture needle 3 is fitted to the through-hole 11a and a large tensile force is acting on the distal-end wire 18a, the swing member 24 is held so as not to be moved in the longitudinal axial direction.

With this embodiment, because, in this state, the tensile-force adjusting mechanisms 32 are in the state shown in FIG. 7C, the large tensile forces FC are exerted on the distal-end wires 18a, 18b, and thus, the holding members 16, 17 are maintained in a state in which the holding members 16, 17 are biased toward the proximal end side.

In this state, the suture device 1 according to this embodiment is inserted, from the treatment portion 8 side, into the channel 5b from an insertion port positioned on the base-end side of the insertion portion 5 disposed outside the body, and the treatment portion 8 is made to protrude from the distal-end surface of the insertion portion 5. By doing so, the treatment portion 8 is also disposed in the visual field range of the observation optical system 5c of the endoscope 4.

Figure 11A:
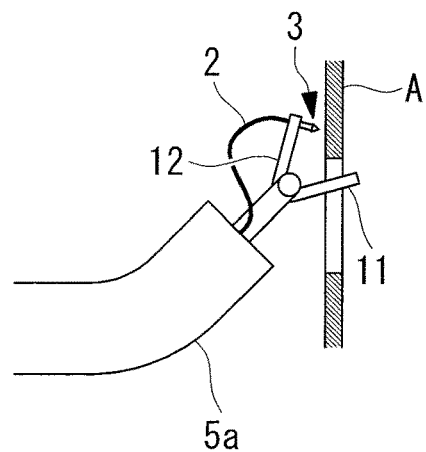
FIG. 11A is a diagram for explaining, sequentially, procedures involved in a tissue suturing operation of the suture device according to this embodiment.

The tissue A, that is, the site to be sutured, is disposed in the area in front of the treatment portion 8 while checking the endoscope image; the opening/closing wire 14 is pushed in toward the distal end side by manipulating the handles 21a of the opening/closing manipulating portion 21; and the two gripping members 11, 12 are pivoted via the linkages 13 and disposed in positions at which the gripping members 11, 12 are separated from each other, as shown in FIGS. 8 and 11A. Because the holding member 17 on the pointed end portion 3a side has the suture needle 3 in a released state and the holding member 16 on the flange portion 3d side has the suture needle 3 fixed to the gripping member 11, the two gripping members 11, 12 are opened in a state in which the pointed end portion 3a of the suture needle 3 protrudes inward.

In this case, when the two gripping members 11, 12 are pivoted about the pivot 10a by large angles, the distal-end wires 18a, 18b having high rigidities are bent at large radii of curvature. As a result, because the distal-end wires 18a, 18b travel in shortcut paths without passing through the center of the pivot, the path lengths are changed. In this embodiment, because the tensile-force adjusting mechanisms 32 bias the swing member 24 toward the proximal end side by large tensile forces FC, when the distal-end wires 18a, 18b are bent by opening the gripping members 11, 12, as shown in FIG. 6C, the tensile forces FC cause the swing member 24 to be moved toward the proximal end side. By doing so, slackening of the distal-end wires 18a, 18b caused by the changes in the path lengths is prevented, and thus, the holding member 16 is maintained in the state in which the holding member 16 is inserted into the recessed portion 3c of the suture needle 3.

In other words, with the suture device 1 according to this embodiment, it is possible to stably hold the suture needle 3 without causing the suture needle 3 to fall out of the through-holes 11a, 12a even if the two gripping members 11, 12 are widely opened, and thus, there is an advantage in that it is possible to perform suturing by gripping thicker tissue A between the gripping members 11, 12.

Next, the treatment portion 8 is moved forward to a position at which the tissue A is sandwiched between the two gripping members 11, 12, the opening/closing wire 14 is pulled back toward the proximal end side by manipulating the opening/closing manipulating portion 21, and the two gripping members 11, 12 are closed via the linkages 13. By doing so, as shown in FIG. 9, the pointed end portion 3a of the suture needle 3 pierces through the tissue A from one side thereof and is inserted into the through-hole 11a of the other gripping member 11 disposed on the other side, and thus, the tissue A is sandwiched between the two gripping members 11, 12.

Figure 9:
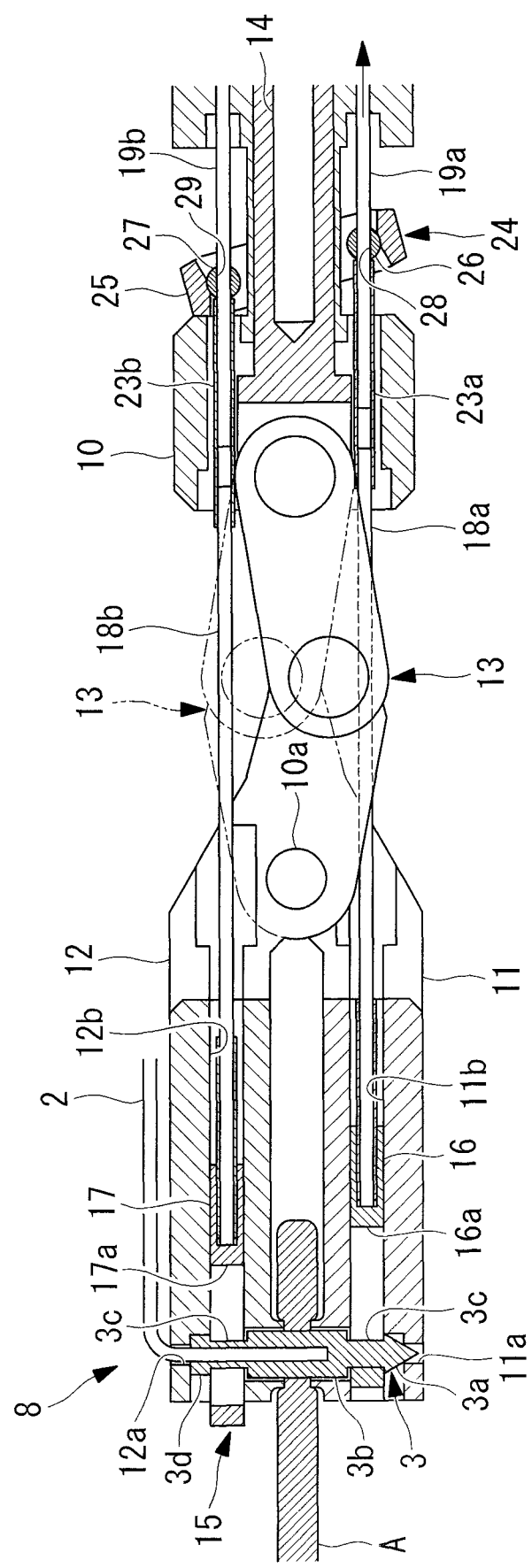
FIG. 9 is a longitudinal cross-sectional view showing a state in which, from the state shown in FIG. 8, the two gripping members are closed, tissue is penetrated by the suture needle, and the holding member holding the suture needle is switched.
Figure 11B:
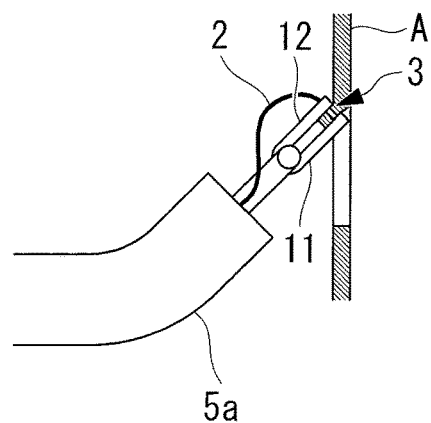
FIG. 11B is a diagram for explaining, sequentially, the procedures involved in the tissue suturing operation of the suture device according to this embodiment.

In this state, when a tensile force is exerted on the driving wire 19a that pulls the holding member 16 on the pointed end portion 3a side by manipulating the handles 22a of the passing manipulating portion 22, the tensile force is transmitted to the driving wire 19a from the handles 22a, the holding member 16 on the pointed end portion 3a side is pulled, and thus, as shown in FIGS. 9 and 11B, the holding member 16 is inserted into the recessed portion 3c on the pointed end portion 3a side. On the other hand, the holding member 17 on the flange portion 3d side is moved forward due to swinging of the swing member 24, thus releasing the suture needle 3.

Figure 10:
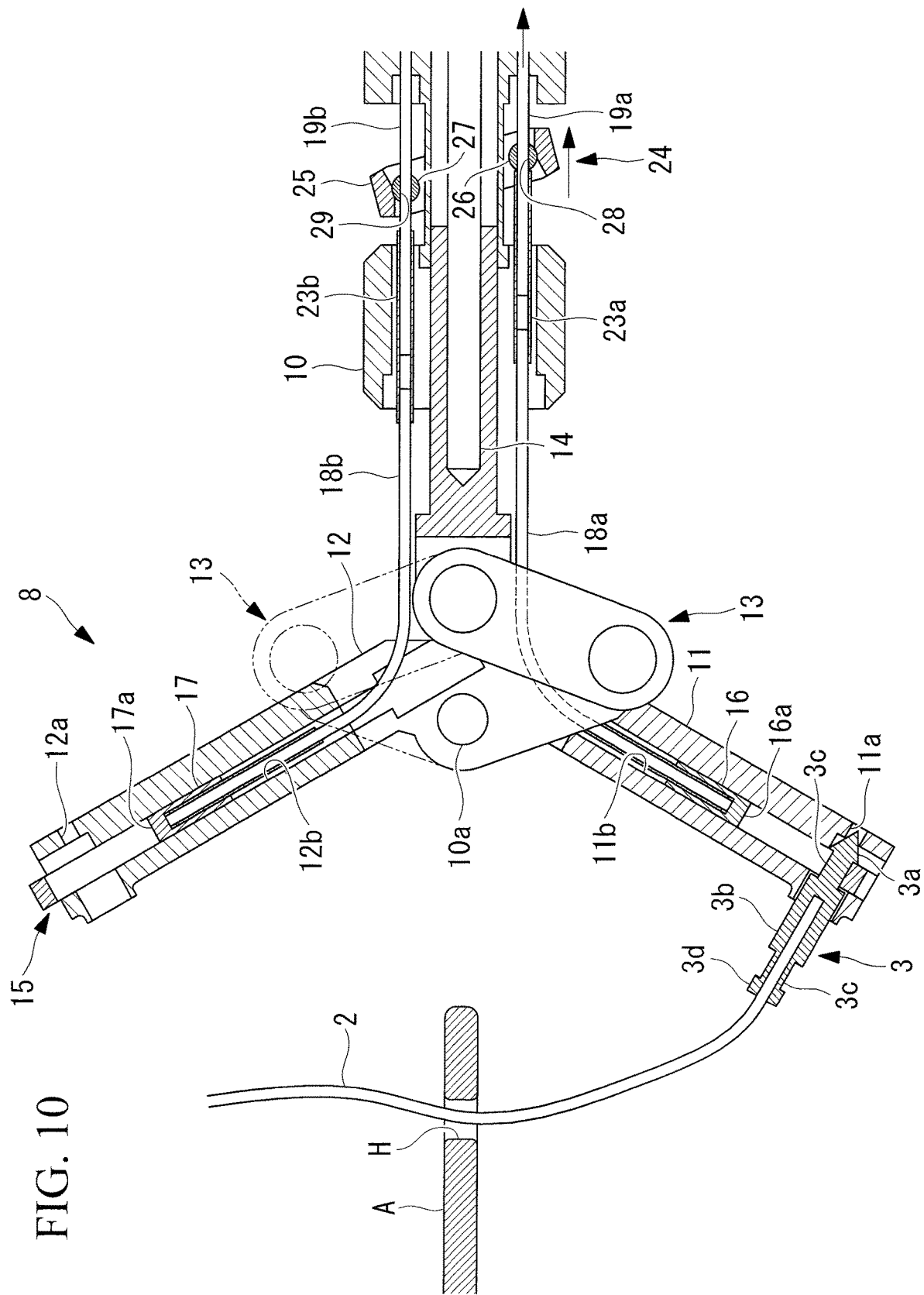
FIG. 10 is a longitudinal cross-sectional view showing a state in which, from the state shown in FIG. 9, the two gripping members are opened again.
Figure 11C:
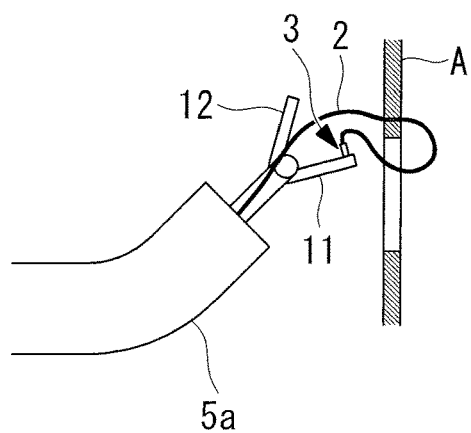
FIG. 11C is a diagram for explaining, sequentially, the procedures involved in the tissue suturing operation of the suture device according to this embodiment.

Then, the opening/closing wire 14 is pushed in toward the distal end side by manipulating the handles 21a of the opening/closing manipulating portion 21 again, and thus, the two gripping members 11, 12 are opened via the linkages 13. Because the holding member 17 on the flange portion 3d side has the suture needle 3 in a released state and the holding member 16 on the pointed end portion 3a side has the suture needle 3 fixed to the gripping member 11, the two gripping members 11, 12 are opened, as shown in FIGS. 10 and 11C, in a state in which the flange portion 3d of the suture needle 3 protrudes inward.

In this case also, it is possible to stably hold the suture needle 3 without causing the suture needle 3 to fall out of the through-holes 11a, 12a even if the two gripping members 11, 12 are widely opened.

Figure 11D:
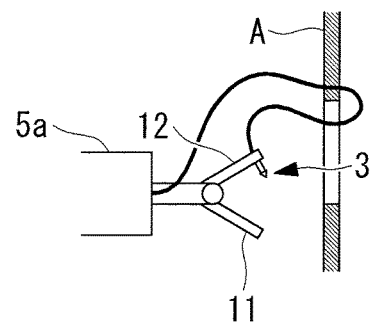
FIG. 11D is a diagram for explaining, sequentially, the procedures involved in the tissue suturing operation of the suture device according to this embodiment.

By doing so, because the suture needle 3 passes through a hole H made in the tissue A, the suture thread 2 is made to pass through the tissue A through the hole H. In this state, because the suture needle 3 is held by the gripping member 11 such that the flange portion 3d is protruded, by transferring the suture needle 3 to one gripping member 12 by means of the passing mechanism 15 by opening/closing the two gripping members 11, 12 at a position at which the tissue A is not sandwiched therebetween (empty gripping), as shown in FIG. 11D, it is possible to again hold the suture needle 3 in the gripping member 12 in a state in which the pointed end portion 3a is protruded.

Figure 11E:
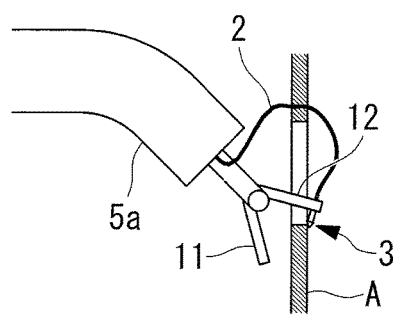
FIG. 11E is a diagram for explaining, sequentially, the procedures involved in the tissue suturing operation of the suture device according to this embodiment.
Figure 11F:
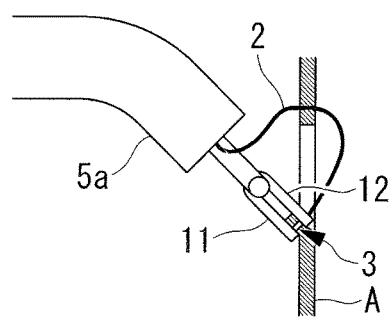
FIG. 11F is a diagram for explaining, sequentially, the procedures involved in the tissue suturing operation of the suture device according to this embodiment.
Figure 11G:
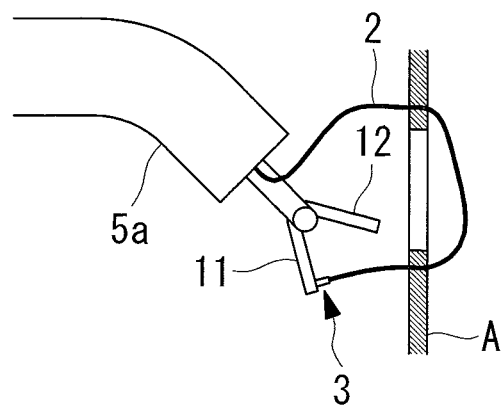
FIG. 11G is a diagram for explaining, sequentially, the procedures involved in the tissue suturing operation of the suture device according to this embodiment.

Then, as shown in FIGS. 11E to 11G, by repeating the above-described procedures after changing the location at which the suture thread 2 is made to penetrate through the tissue A, it is possible to make the suture thread 2 penetrate through the tissue A at two or more locations, as shown in FIG. 11G. Subsequently, by pulling the suture thread 2, the tissue A is tightened, thus completing suturing.

As has been described above, with the suture device 1 according to this embodiment, because slackening of the distal-end wires 18a, 18b due to changes in the path lengths is prevented even when the two gripping members 11, 12 are widely opened and the holding member 16, 17 is maintained in the state in which the holding member 16, 17 is inserted into the recessed portions 3c of the suture needle 3, there is an advantage in that it is possible to smoothly perform the opening/closing operation of the gripping members 11, 12 and the passing operation of the suture needle 3.

Note that, with this embodiment, because the tensile-force adjusting mechanisms 32 are individually provided at the intermediate positions on the two driving wires 19a, 19b, it is possible to automatically adjust the tensile forces FA and FB exerted on the driving wires 19a, 19b when swinging the swing member 24 and the tensile forces FC exerted on the driving wires 19a, 19b when opening the two gripping members 11, 12.

Alternatively, the operator may adjust the tensile forces exerted on the driving wires 19a, 19b in accordance with the pivoting angles of the gripping members 11, 12 without providing the tensile-force adjusting mechanisms 32 on the driving wires 19a, 19b.

From the above-described embodiments, the following aspects of the present invention are derived.

An aspect of the present disclosure is a suture device including: an elongated shaft member that extends along a longitudinal axis and that is flexible and tubular; a pair of two gripping members that are disposed at a distal end side of the elongated shaft member in a pivotable manner about a pivot orthogonal to the longitudinal axis so that the two gripping members are opened/closed; and a passing mechanism configured to pass a suture needle between the gripping members, the suture needle to which a suture thread is attached, wherein the passing mechanism comprises: fitting holes that are respectively provided in the individual gripping members along opening/closing directions thereof and into which the suture needle is fitted; holding members which are respectively provided in the gripping members so as to be movable in the directions that intersect axes of the individual fitting holes, and each of which is inserted into a recessed portion provided in an outer circumferential surface of the suture needle fitted into the fitting hole when the holding member is pulled toward a proximal end side; a swing member which is provided at a position that is closer to a proximal-end side of the elongated shaft member than the pivot of the gripping members so as to be swingable about a swing axis that is orthogonal to the longitudinal axis;

a pair of tensile-force transmitting members which extend inside the elongated shaft member and which transmit tensile force for swinging the swing member; axial-force transmitting members which have flexibility, which is disposed between the swing member and the respective holding members, and which respectively transmit axial force based on swing of the swing member in order to oppositely move the holding members; and a hold-state maintaining mechanism that maintains the holding members in a state in which one of the holding members is inserted into the recessed portion regardless of pivoting of the gripping members.

With this aspect, the suture needle is held in the fitting hole of one of the gripping members in a state in which the suture needle is fitted thereto with the pointed end portion thereof pointing toward the other gripping member.

When the two gripping members are closed so as to grip a suture object therebetween, the suture needle penetrates through the suture object and is fitted to the fitting hole of the other gripping member. In this state, by means of the passing mechanism, holding of the suture needle by the one of the gripping members is released, the suture needle is held by the other gripping member, and by opening the two gripping members, it is possible to pass the suture needle to the other gripping member from said one gripping member, and to make the suture thread attached to the suture needle penetrate the suture object.

In this case, holding of the suture needle by respective gripping member is performed by swinging the swing member, which is disposed closer to the proximal-end side than the pivot of the gripping member is, by means of the tensile force exerted on the tensile-force transmitting member on the proximal-end side of the elongated shaft member. In other words, by means of the axial-force transmitting member, axial forces formed by tensile forces or compressive forces are made to act on the two holding members in association with swinging of the swing member, thus moving the two holding members in directions that intersect the axes of the fitting holes and in opposing directions from each other, and thus, said one holding member is inserted into the recessed portion on the suture needle supported in a state in which the suture needle is fitted into the fitting hole, and the other holding member is removed from the recessed portion.

By inserting the holding member into the recessed portion, a side wall of the recessed portion and the holding member engage with each other in a length direction of the suture needle, thus engaging the suture needle so as not to move in the axial direction of the fitting hole. When the two gripping members are opened in this state, the suture needle is held in a state in which the suture needle is fitted in the fitting hole of said one gripping member with the pointed end pointing toward the other gripping member.

Because the holding members are moved by means of the tensile forces, flexible wires or the like are employed as the tensile-force transmitting members that pass through the inside of the flexible elongated shaft member, and, by preventing malfunction of the holding members due to slacking and buckling of the tensile-force transmitting members, it is possible to stably hold the suture needle.

In addition, when the two gripping members are widely opened, the axial-force transmitting members having flexibility are bent, and the path lengths thereof are changed; however, because the state in which a holding member is inserted into the recessed portion is maintained by means of the hold-state maintaining mechanism, it is possible to stably hold the suture needle without causing the suture needle to fall out of the fitting hole.

In the above-described aspect, the swing member may be movable in the longitudinal axis, the hold-state maintaining mechanism may be provided with a resilient member that biases the swing member toward a distal end side, and the hold-state maintaining mechanism may be configured to allow the swing member to move toward a proximal-end side along the longitudinal axis when a tensile force applied on one of the tensile-force transmitting members exceeds a tensile force for causing the swing member to swing and biasing force exerted by the resilient member.

By doing so, by exerting tensile forces on the tensile-force transmitting members on the proximal-end side of the elongated shaft member, the swing member is swung, the suture needle is held by the holding member of the one of the gripping members, and the suture needle is released from the holding member of the other gripping member. When the two gripping members are opened in this state, the axial-force transmitting members are bent and the path lengths thereof are changed; however, because, when even greater tensile forces act on the tensile-force transmitting members, the swing member is moved toward the proximal-end side in the longitudinal axial direction against the biasing force exerted thereon by the resilient member, it is possible to maintain the state in which the holding member is inserted into the recessed portion and absorbing the changes in the path lengths by moving the proximal-ends of the axial-force transmitting members toward the proximal-end side.

In the above-described aspect, each tensile-force transmitting member may be provided with a tensile-force adjusting mechanism which transmits tensile force that is less than ½ the biasing force exerted by the resilient member to the swing member and the axial-force transmitting member when making the swing member swing, and which transmits tensile force that is greater than the biasing force exerted by the resilient member to the swing member and the axial-force transmitting member when having made the swing member swing.

By doing so, when swinging the swing member, the swing member is swung while maintaining the position thereof on the most-distal-end side; after the swing member is swung, the swing member is moved toward the proximal-end side by deforming the resilient member; and thus, it is possible to maintain the suture needle in the state in which the suture needle is held.

In the above-described aspect, the tensile-force adjusting mechanism may be provided with a movable member that is fixed to the tensile-force transmitting member, first compression spring that is disposed between the movable member and a casing and second compression spring that starts to be compressed between the movable member and the casing during deformation of the first compression spring.

By doing so, when the tensile forces are exerted on the tensile-force transmitting members, the movable members are moved with respect to the casing and the first compression springs are compressed, tensile forces that are less than ½ the biasing force exerted by the resilient member are transmitted to the swing member and the axial-force transmitting members, and thus, the swing member is swung. Then, when even greater tensile forces are exerted on the tensile-force transmitting members, the second compression springs begin to be compressed during displacement of the first compression springs, which makes the tensile forces transmitted to the swing member and the tensile-force transmitting members equal to the sum of the biasing forces exerted by the two types of compression springs, thus exceeding the biasing force exerted by the resilient member.

By doing so, the tensile forces transmitted to the swing member and the axial-force transmitting members from the tensile-force transmitting members are automatically adjusted. Thus, even if the two gripping members are opened in the state in which the biasing forces are generated by the two types of compression springs, thereby bending the axial-force transmitting members and changing the pathway lengths thereof, the changes in the pathway lengths are absorbed by moving the proximal-end sides of the axial-force transmitting members by automatically moving the swing member toward the proximal-end side by the biasing force that is equal to the sum of the biasing forces exerted by the two types of compression springs, and thus, it is possible to maintain the holding member in the state in which the holding member is inserted into the recessed portion.

In the above-described aspect, the tensile-force transmitting members may be respectively connected to the axial-force transmitting members, the swing member may be provided with through-holes through which the tensile-force transmitting members are made to pass, in a movable manner, along the longitudinal axis, and stopper portions may be respectively secured to the tensile-force transmitting members at positions that are closer to the distal end side than the swing member and that cannot pass through the through-holes.

By doing so, when the tensile force is exerted on one of the tensile-force transmitting members, the tensile force is directly transmitted to one of the axial-force transmitting members, one of the holding members is moved toward the base end, the tensile force is transmitted to the swing member because the stopper portion cannot pass through the through-hole and is caught therein, and thus, the swing member is swung. By doing so, the stopper portion provided on the other tensile-force transmitting member is pushed out toward the distal end by the swing member, the compressive force thereof is transmitted by the other axial-force transmitting member, and thus, the other holding member is moved toward the distal end. In other words, by means of simple structures, the two holding members are moved in directions that intersect the axes of the fitting holes and in directions opposing each other, said one holding member is inserted into the recessed portion of the suture needle, which is supported in the state in which the suture needle is fitted to the fitting hole and the other holding member is removed from the other recessed portion, and thus, it is possible to easily transfer the suture needle.

The aforementioned aspects afford an advantage in that it is possible to smoothly perform an opening/closing operation of gripping members and a transferring operation of a suture needle.

REFERENCE SIGNS LIST 1 suture device
2 suture thread
3 suture needle
3c recessed portion
7 elongated shaft member
10a pivot
11, 12 gripping member
11a, 12a through-hole (fitting hole)
15 passing mechanism
16, 17 holding member
18a, 18b distal-end wire (axial-force transmitting member)
19a, 19b driving wire (tensile-force transmitting member)
23a, 23b connecting member (stopper portion)
24 swing member
28, 29 through-hole
31 compression coil spring (resilient member)
32 tensile-force adjusting mechanism (hold-state maintaining mechanism)
34 first movable member (movable member)
35 first compression coil spring (first compression spring)
37 second compression coil spring (second compression spring)

The invention claimed is:

1. A suture device comprising:
an elongated shaft member that extends along a longitudinal axis and that is flexible and tubular;
a pair of gripping members that are disposed at a distal end side of the elongated shaft member in a pivotable manner about a pivot orthogonal to the longitudinal axis, the pair of gripping members comprising a first gripping member and a second gripping member; and
a passing mechanism configured to pass a suture needle between the first gripping member and the second gripping member, the suture needle being configured to attach a suture thread, wherein
the passing mechanism comprises:
first and second fitting holes provided in the first and second gripping members, respectively, the suture needle being fitted into the first and second fitting holes;
a first holding member provided in the first gripping member so as to be movable in a direction that intersects an axis of the first fitting hole, the first holding member being inserted into a first recessed portion provided in an outer circumferential surface of the suture needle fitted into the first fitting hole when the first holding member is pulled toward a proximal end side;
a second holding member provided in the second gripping member so as to be movable in a direction that intersects an axis of the second fitting hole, the second holding member being inserted into a second recessed portion provided in the outer circumferential surface of the suture needle fitted into the second fitting hole when the second holding member is pulled toward the proximal end side;
a swing member provided at a position that is closer to a proximal end side of the elongated shaft member than the pivot so as to be swingable about a swing axis that is orthogonal to the longitudinal axis;
tensile-force transmitting members extending inside the elongated shaft member, the tensile-force transmitting members transmitting a tensile force for swinging the swing member;
axial-force transmitting members that have flexibility and are disposed between the swing member and the first and second holding members, the axial-force transmitting members transmitting an axial force based on a swing of the swing member in order to oppositely move the first and second holding members; and
a hold-state maintaining mechanism that maintains the first and second holding members in a state in which one of the first and second holding members is inserted into the corresponding recessed portion regardless of pivoting of the first and second gripping members,
wherein the swing member is movable in a longitudinal axis direction, the hold-state maintaining mechanism is provided with a resilient member that biases the swing member toward a distal end side, and the hold-state maintaining mechanism is configured to allow the swing member to move toward the proximal end side along the longitudinal axis when a tensile force applied on one of the tensile-force transmitting members exceeds a tensile force for causing the swing member to swing and a biasing force exerted by the resilient member.

2. The suture device according to claim 1, wherein each tensile-force transmitting member is provided with a tensile-force adjusting mechanism that transmits tensile force that is less than ½ the biasing force exerted by the resilient member to the swing member and a corresponding one of the axial-force transmitting members when making the swing member swing, and that transmits tensile force that is greater than the biasing force exerted by the resilient member to the swing member and the corresponding one of the axial-force transmitting members when having made the swing member swing, and wherein the tensile-force adjusting mechanism comprises a movable member fixed to the corresponding one of the tensile-force transmitting members, a first compression spring disposed between the movable member and a casing, and a second compression spring configured to start to be compressed between the movable member and the casing during deformation of the first compression spring.

3. The suture device according to claim 1, wherein the tensile-force transmitting members are respectively connected to the axial-force transmitting members, the swing member is provided with through-holes through which the tensile-force transmitting members are made to pass, in a movable manner, along the longitudinal axis, and stopper portions are respectively secured to the tensile-force transmitting members at positions that are closer to the distal end side than the swing member and that cannot pass through the through-holes.

4. A suture device comprising:

an elongated shaft member that extends along a longitudinal axis and that is flexible and tubular;

a pair of gripping members that are disposed at a distal end side of the elongated shaft member in a pivotable manner about a pivot orthogonal to the longitudinal axis, the pair of gripping members comprising a first gripping member and a second gripping member; and a passing mechanism configured to pass a suture needle between the first gripping member and the second gripping member, the suture needle being configured to attach a suture thread, wherein the passing mechanism comprises:

first and second fitting holes provided in the first and second gripping members, respectively, the suture needle being fitted into the first and second fitting holes;

a first holding member provided in the first gripping member so as to be movable in a direction that intersects an axis of the first fitting hole, the first holding member being inserted into a first recessed portion provided in an outer circumferential surface of the suture needle fitted into the first fitting hole when the first holding member is pulled toward a proximal end side;

a second holding member provided in the second gripping member so as to be movable in a direction that intersects an axis of the second fitting hole, the second holding member being inserted into a second recessed portion provided in the outer circumferential surface of the suture needle fitted into the second fitting hole when the second holding member is pulled toward the proximal end side;

a swing member provided at a position that is closer to a proximal end side of the elongated shaft member than the pivot so as to be swingable about a swing axis that is orthogonal to the longitudinal axis;

tensile-force transmitting members extending inside the elongated shaft member, the tensile-force transmitting members transmitting a tensile force for swinging the swing member;

axial-force transmitting members that have flexibility and are disposed between the swing member and the first and second holding members, the axial-force transmitting members transmitting an axial force based on a swing of the swing member in order to oppositely move the first and second holding members; and a hold-state maintaining mechanism that maintains the first and second holding members in a state in which one of the first and second holding members is inserted into the corresponding recessed portion regardless of pivoting of the first and second gripping members.

* * * * *